(12) United States Patent
Collazo

(10) Patent No.: US 7,785,371 B2
(45) Date of Patent: Aug. 31, 2010

(54) MODULAR HUMERAL HEAD

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 12/421,756

(22) Filed: Apr. 10, 2009

(65) Prior Publication Data
US 2009/0192624 A1    Jul. 30, 2009

Related U.S. Application Data

(62) Division of application No. 11/599,602, filed on Nov. 13, 2006, now Pat. No. 7,537,618.

(51) Int. Cl.
*A61F 2/40* (2006.01)
(52) U.S. Cl. .............. 623/19.14; 623/19.11; 623/23.42; 623/23.47
(58) Field of Classification Search .............. 623/16.11, 623/18.11, 19.11–19.14, 23.11, 23.42, 23.47; 606/251–253, 266, 287
See application file for complete search history.

(56) References Cited

U.S. PATENT DOCUMENTS

| 2,682,265 A | 6/1954 | Collison |
| 2,719,522 A | 10/1955 | Hudack |
| 2,765,787 A | 10/1956 | Pellet |
| 2,781,758 A | 2/1957 | Chevalier |
| 2,785,673 A | 3/1957 | Anderson |
| 3,064,645 A | 11/1962 | Ficat et al. |
| 3,067,740 A | 12/1962 | Haboush |
| 3,102,536 A | 9/1963 | Rose |
| 3,658,056 A | 4/1972 | Huggler et al. |

(Continued)

FOREIGN PATENT DOCUMENTS

DE    2015324    11/1971

(Continued)

OTHER PUBLICATIONS

Partial European Search Report, EP 07120601, dated Apr. 3, 2009.

(Continued)

*Primary Examiner*—David H Willse
*Assistant Examiner*—Megan Wolf
(74) *Attorney, Agent, or Firm*—Lerner, David, Littenberg, Krumholz & Mentlik, LLP

(57) ABSTRACT

A modular humeral head system includes a housing having an outer surface and an inner surface. A hemispherical socket formed on one end of the inner surface and threads formed on the other end of the inner surface. A cap is attached at the threaded end of the housing. The cap has one or more threaded holes that run from the top surface to bottom surface of the cap. A screw may be inserted in each hole. The modular humeral head system also includes an intermediate piece having a hemispherical head at one end of a tapered shaft. The tapered shaft is inserted in a humeral stem. The hemispherical head and the hemispherical socket form a ball and socket coupling. A trial head may be impacted on the housing. The trial head has one or more holes that are aligned with the screws inserted in the cap.

33 Claims, 11 Drawing Sheets

U.S. PATENT DOCUMENTS

| | | | |
|---|---|---|---|
| 3,670,724 A | 6/1972 | Bosacco | |
| 3,694,820 A | 10/1972 | Scales et al. | |
| 3,782,373 A | 1/1974 | Smythe | |
| 3,803,641 A | 4/1974 | Golyakhovsky et al. | |
| 3,806,957 A | 4/1974 | Shersher et al. | |
| 3,814,089 A | 6/1974 | Deyerle | |
| 3,818,512 A | 6/1974 | Shersher et al. | |
| 3,859,669 A | 1/1975 | Shersher et al. | |
| 3,863,273 A | 2/1975 | Averill | |
| 3,874,003 A | 4/1975 | Moser et al. | |
| 3,906,550 A | 9/1975 | Rostoker et al. | |
| 3,916,451 A | 11/1975 | Buechel et al. | |
| 3,918,441 A | 11/1975 | Getscher | |
| 3,974,527 A | 8/1976 | Shersher et al. | |
| 3,979,778 A | 9/1976 | Stroot | |
| 3,987,499 A | 10/1976 | Scharbach et al. | |
| 4,004,300 A | 1/1977 | English et al. | |
| 4,030,143 A | 6/1977 | Elloy et al. | |
| 4,040,131 A | 8/1977 | Gristina | |
| 4,042,980 A | 8/1977 | Swanson et al. | |
| 4,051,559 A | 10/1977 | Pifferi et al. | |
| 4,115,875 A | 9/1978 | Rambert et al. | |
| 4,261,062 A | 4/1981 | Amstutz et al. | |
| 4,404,691 A | 9/1983 | Buning et al. | |
| 4,406,023 A | 9/1983 | Harris | |
| 4,430,761 A | 2/1984 | Niederer et al. | |
| 4,459,708 A | 7/1984 | Buttazzoni et al. | |
| 4,488,319 A | 12/1984 | von Recum | |
| 4,532,660 A | 8/1985 | Field et al. | |
| 4,550,450 A | 11/1985 | Kinnett | |
| 4,578,081 A | 3/1986 | Harder et al. | |
| 4,624,674 A | 11/1986 | Pappas et al. | |
| 4,645,506 A | 2/1987 | Link et al. | |
| 4,655,778 A | 4/1987 | Koeneman | |
| 4,676,797 A | 6/1987 | Anapliotis et al. | |
| 4,693,723 A | 9/1987 | Gabard et al. | |
| 4,693,724 A | 9/1987 | Rhenter et al. | |
| 4,698,063 A | 10/1987 | Link et al. | |
| 4,822,370 A | 4/1989 | Schelhas et al. | |
| 4,840,632 A | 6/1989 | Kampner | |
| 4,842,606 A | 6/1989 | Kranz et al. | |
| 4,865,605 A | 9/1989 | Dines et al. | |
| 4,865,609 A | 9/1989 | Roche | |
| 4,895,572 A | 1/1990 | Chernoff | |
| 4,904,266 A | 2/1990 | Barber | |
| 4,908,032 A | 3/1990 | Keller et al. | |
| 4,919,669 A | 4/1990 | Lannelongue et al. | |
| 4,919,670 A | 4/1990 | Dale et al. | |
| 4,932,974 A | 6/1990 | Pappas et al. | |
| 4,959,066 A | 9/1990 | Dunn et al. | |
| 4,963,155 A | 10/1990 | Lazzeri et al. | |
| 4,986,833 A | 1/1991 | Worland | |
| 4,995,883 A | 2/1991 | Demane et al. | |
| 5,002,580 A | 3/1991 | Noble et al. | |
| 5,002,581 A | 3/1991 | Paxson et al. | |
| 5,030,234 A | 7/1991 | Pappas et al. | |
| 5,032,130 A | 7/1991 | Schelhas et al. | |
| 5,074,879 A | 12/1991 | Pappas et al. | |
| 5,080,676 A | 1/1992 | May et al. | |
| 5,080,685 A | 1/1992 | Bolesky et al. | |
| 5,108,437 A | 4/1992 | Kenna | |
| 5,108,452 A | 4/1992 | DeMane et al. | |
| 5,116,379 A | 5/1992 | McLardy-Smith et al. | |
| 5,135,529 A | 8/1992 | Paxson et al. | |
| 5,169,401 A | 12/1992 | Lester et al. | |
| 5,181,928 A | 1/1993 | Bolesky et al. | |
| 5,207,682 A | 5/1993 | Cripe | |
| 5,261,915 A | 11/1993 | Durlacher et al. | |
| 5,282,865 A | 2/1994 | Dong | |
| 5,286,260 A | 2/1994 | Bolesky et al. | |
| 5,314,479 A | 5/1994 | Rockwood, Jr. et al. | |
| 5,336,268 A | 8/1994 | Rispeter | |
| 5,342,363 A | 8/1994 | Richelsoph | |
| 5,358,526 A | 10/1994 | Tornier et al. | |
| 5,370,706 A | 12/1994 | Bolesky et al. | |
| 5,405,403 A | 4/1995 | Mikhail | |
| 5,489,309 A | 2/1996 | Lackey et al. | |
| 5,507,817 A | 4/1996 | Craig et al. | |
| 5,507,818 A | 4/1996 | McLaughlin | |
| 5,549,682 A | 8/1996 | Roy | |
| 5,580,352 A | 12/1996 | Sekel | |
| 5,591,233 A | 1/1997 | Kelman et al. | |
| 5,645,548 A | 7/1997 | Augsburger | |
| 5,645,607 A | 7/1997 | Hickey | |
| 5,658,340 A | 8/1997 | Muller et al. | |
| 5,662,651 A | 9/1997 | Tornier et al. | |
| 5,702,447 A | 12/1997 | Walch et al. | |
| 5,702,457 A | 12/1997 | Walch et al. | |
| 5,741,335 A | 4/1998 | Gerber et al. | |
| 5,779,709 A | 7/1998 | Harris, Jr. et al. | |
| 5,788,700 A | 8/1998 | Morawa et al. | |
| 5,792,143 A | 8/1998 | Samuelson et al. | |
| 5,800,560 A | 9/1998 | Draenert | |
| 5,860,982 A | 1/1999 | Ro et al. | |
| 5,910,171 A | 6/1999 | Kummer et al. | |
| 6,129,764 A | 10/2000 | Servidio | |
| 6,171,341 B1 | 1/2001 | Boileau et al. | |
| 6,193,758 B1 | 2/2001 | Huebner | |
| 6,197,062 B1 | 3/2001 | Fenlin | |
| 6,197,063 B1 | 3/2001 | Dews | |
| 6,520,994 B2 | 2/2003 | Nogarin | |
| 6,589,282 B2 | 7/2003 | Pearl | |
| 6,673,115 B2 | 1/2004 | Resch et al. | |
| 6,676,705 B1 | 1/2004 | Wolf | |
| 6,719,799 B1 | 4/2004 | Kropf et al. | |
| 6,736,851 B2 | 5/2004 | Maroney et al. | |
| 6,736,852 B2 | 5/2004 | Callaway et al. | |
| 6,749,637 B1 | 6/2004 | Bahler et al. | |
| 6,776,799 B2 | 8/2004 | Ball et al. | |
| 6,821,300 B2 | 11/2004 | Masini | |
| 6,863,690 B2 | 3/2005 | Ball et al. | |
| 6,887,277 B2 | 5/2005 | Rauscher et al. | |
| 6,942,699 B2 | 9/2005 | Stone et al. | |
| 7,097,663 B1 | 8/2006 | Nicol et al. | |
| 7,175,663 B1 | 2/2007 | Stone | |
| 7,229,478 B2 | 6/2007 | Masini | |
| 2004/0044347 A1* | 3/2004 | Cassell | 606/92 |
| 2005/0234457 A1 | 10/2005 | James et al. | |
| 2005/0288681 A1 | 12/2005 | Klotz et al. | |
| 2007/0100458 A1 | 5/2007 | Dalla Pria | |

FOREIGN PATENT DOCUMENTS

| | | |
|---|---|---|
| DE | 2400650 | 7/1974 |
| DE | 3023354 | 4/1981 |
| DE | 3329978 | 3/1985 |
| DE | 3415934 | 10/1985 |
| DE | 4320086 | 12/1994 |
| DE | 19548154 | 6/1997 |
| DE | 10123517 | 11/2002 |
| EP | 0 000 549 | 2/1979 |
| EP | 0 017 743 | 10/1980 |
| EP | 0 098 224 | 1/1984 |
| EP | 0 145 939 | 6/1985 |
| EP | 0 163 121 | 12/1985 |
| EP | 0 190 981 | 8/1986 |
| EP | 0 198 163 | 10/1986 |
| EP | 0 201 407 | 11/1986 |
| EP | 0 243 298 | 10/1987 |
| EP | 0 278 807 | 8/1988 |
| EP | 0 339 530 | 11/1989 |
| EP | 0 393 608 | 10/1990 |
| EP | 0 501 207 | 9/1992 |
| EP | 0 611 225 | 8/1994 |

| | | |
|---|---|---|
| EP | 0 617 934 | 10/1994 |
| EP | 0 622 062 | 11/1994 |
| EP | 0 634 154 | 1/1995 |
| EP | 0 639 359 | 2/1995 |
| EP | 0 679 375 | 11/1995 |
| EP | 0 715 836 | 6/1996 |
| EP | 1402856 | 3/2004 |
| FR | 2225141 | 11/1974 |
| FR | 2567019 | 1/1986 |
| FR | 2574283 | 6/1986 |
| FR | 2576793 | 8/1986 |
| FR | 2579454 | 10/1986 |
| FR | 2606273 | 5/1988 |
| FR | 2619502 | 2/1989 |
| FR | 2634371 | 1/1990 |
| FR | 2652498 | 4/1991 |
| FR | 2664809 | 1/1992 |
| FR | 2689756 | 10/1993 |
| FR | 2689757 | 10/1993 |
| FR | 2689758 | 10/1993 |
| FR | 2699400 | 6/1994 |
| FR | 2705558 | 12/1994 |
| FR | 2737107 | 1/1997 |
| FR | 2773469 | 7/1999 |
| GB | 1521679 | 8/1978 |
| GB | 1531487 | 11/1978 |
| SU | 1279629 | 12/1986 |
| WO | 0122905 | 4/2001 |
| WO | 0239931 | 5/2002 |
| WO | 03096939 | 11/2003 |

OTHER PUBLICATIONS

Equinoxe, operative technique, press-fit, date not known.
Aequalis-reversed, shoulder prosthesis, Thorner, date not known.
Comprehensive fracture stem, Biomet Orthopedics, Inc., Jun. 11, 2003.
Equinoxe shoulder system, Exactech, date not known.
Arrow anatomical shoulder prosthesis, Implants Industrie, date not known.
Anatomical shoulder system surgical technique, Zimmer, date not known.
Arrow shoulder system, Implants Industrie, date not known.
Reverse shoulder prosthesis, surgical technique, date not known.
Aequalis-fracture shoulder prosthesis, surgical technique, Aequalis Fracture, Thorner, date not known.
The Buechel-Pappas total shoulder system, Endotec, date not known.

* cited by examiner

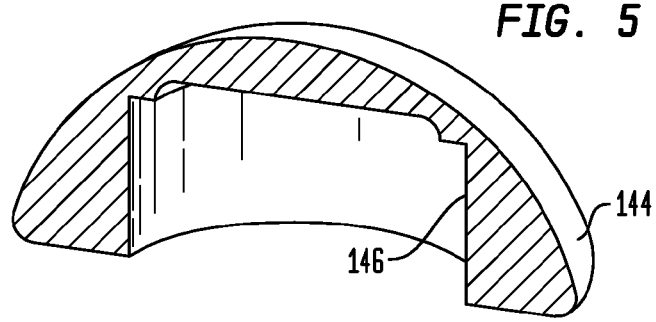
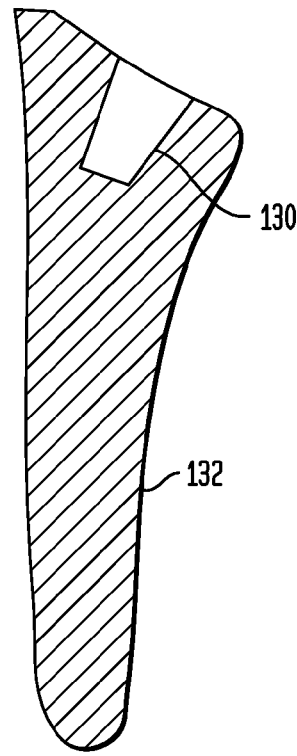
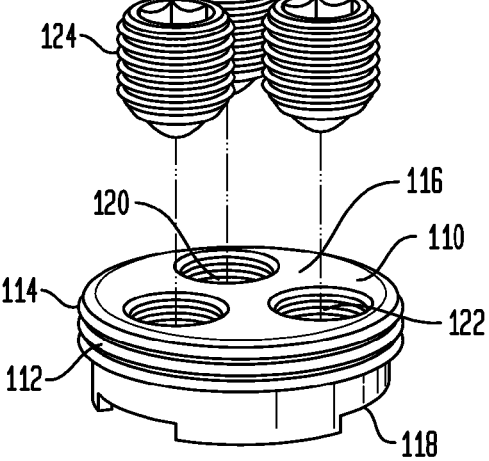
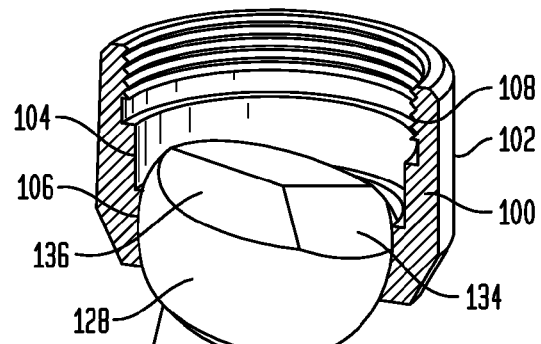
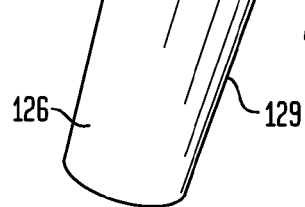

MODULAR HUMERAL HEAD

CROSS-REFERENCE TO RELATED APPLICATION

This application is a divisional of U.S. application Ser. No. 11/599,602, filed Nov. 13, 2006, the entire disclosure of which is hereby incorporated by reference.

BACKGROUND OF THE INVENTION

1. Field of Invention

The present disclosure relates to a prosthetic device system for repairing ball-and-socket type joints in a human body. More particularly the disclosure relates to a modular anatomic adjustable prosthetic device system for the shoulder and hip joints.

2. Description of Prior Art

A joint replacement procedure is sometimes necessary to repair a joint having a diseased or damaged articulating surface. Such a procedure involves removal of the diseased or damaged portions of the joint and replacing them with a prosthetic implant. This is often a desirable procedure for ball-and-socket type joints, particularly the shoulder and hip joints. A shoulder joint replacement procedure, for example, often involves removal of the humeral head and replacement thereof with an implant including a stem and a head. It is important that the implant be positioned correctly within the joint in order to ensure that appropriate joint kinematics, including range of motion, are preserved so as to replicate, as closely as possible, those of the original joint.

The classical prosthetic humeral component is known as the NEER-type and is a one-piece component which is available in many different sizes for replacement of the upper portion of the humerus. The classical humeral component has a stem which is designed to extend downwardly into a cavity formed within the humerus and which is secured with cement or with coatings which promote bone ingrowth to secure the stem. The stem is provided with a generally hemispherical head portion which is configured to replace the head of the organic humerus. However, the orientation of the humeral head relative to the stem varies from patient to patient. Therefore, it is desirable that the orientation of the humeral head be adjustable.

One adjustable device is described in U.S. Pat. No. 5,741,335 to Gerber et al. The shoulder prosthesis of Gerber et al. includes a humeral stem designed to be implanted within the patient's humeral canal and a head portion designed to cooperate with the glenoid cavity of a shoulder. The head portion has a spherical shape generated by revolution about an axis. A spherical socket is formed in the head portion for housing a ball that is fixed to a proximal end of the stem. The axis of revolution of the head portion is off-set with respect to the center of the ball. The assembly formed by the socket and the ball constitutes a joint capable of making the orientation of the head portion vary in relation to the stem by rotation about the center of the ball. The head portion is locked to the stem by a conical push rod which moves into an axial conical bore under the action of a tightening screw. The push rod causes compression of the ball against the spherical cavity by blocked lateral expansion of the ball thereby locking the head portion on the stem.

However, there is a need for prosthetic device system that allow quick and precise adjustment of the position of the humeral head during trial reduction, and once an optimal placement of the humeral head is determined, positively locks the prosthesis in that position.

BRIEF SUMMARY OF THE INVENTION

The modular humeral head system of the present invention overcomes the shortcomings of the prior art. The modular humeral head system includes a housing having an outer surface and an inner surface. A hemispherical socket is formed on one end of the inner surface and threads formed on the other end of the inner surface. The outer surface has a Morse taper. A cap is attached at the threaded end of the housing. The cap has three threaded holes that run from the top surface to bottom surface of the cap. A screw may be inserted in each hole. The head of the screw is formed to allow engagement with a screw driver. The modular humeral head system also includes an intermediate piece having a hemispherical head at one end of a tapered shaft. The tapered shaft has Morse taper that matches a female taper in a humeral stem. Humeral stem may come in different size. A top surface of the hemispherical head has three flat surfaces. These flat surfaces are facing the holes in the cap such that if the screws are advanced in the holes, each screw will contact one flat surface. The hemispherical head and the hemispherical socket form a ball and socket coupling. A trial head may be impacted on the housing. The trial head has three holes that are aligned with the three screws inserted in the cap. These holes provide access to the screws without removing the trial head from the housing.

In use, the assembly of the trial head, cap and housing can be adjusted to be in any angular orientation about hemispherical head. Next, the tapered shaft of the intermediate piece is inserted in the humeral stem to create a modular humeral head assembly for trial reduction of the shoulder joint. The humeral stem is inserted in the prepared medullary canal of humeral bone. With the modular humeral head assembly installed in the medullary canal, the shoulder joint is reduced. The reduced joint is evaluated for being optimal. If any adjustment in the angular location of the trial head is needed, the screws are accessed through holes in the trial head and loosened. Once the screws are loosened, the angular position of the trial head is adjusted and then the screws are tightened. The tightening of the screws fixes the angular position of the trial head. The shoulder joint is evaluated again with the changed position of the trial head, and the process repeated if necessary. Once an optimum position for the trial head is established, the trial head is replaced with a humeral head of corresponding size and shape.

A second embodiment of the modular humeral head system is similar to the above described embodiments in many aspects except that the cap in the second embodiment has one hole. A screw may be inserted in the hole. The modular humeral head system of the second embodiment also includes an intermediate piece having a hemispherical head at one end of a tapered shaft. A top surface of the hemispherical head has a shaped surface. The shaped surface is facing the hole such that if the screw is advanced in the hole, it will contact the shaped surface. The shaped surface and tip of the screw have complimentary shapes. The complimentary surfaces on the tip of screw and the shaped surface allow them to mate in a stable manner. A trial head may be impacted on the housing of the second embodiment. The trial head has one hole that is aligned with the screw inserted in the cap. This hole provides access to the screw without removing the trial head from the housing. The optimum position for the prosthesis is determined in a manner similar to one described in connection with the first embodiment. One difference is that in the second embodiment there is only one screw instead of the three screws in the first embodiment. Once an optimum position for the trial head is established, the trial head is removed. With the trial head removed, bone cement or other bio-compatible material is introduced in a chamber formed between the cap and the hemispherical head. The Bone cement or other bio-compatible material cures in the chamber and turns to a hard mass. The presence of this hard mass in the chamber prevents the housing from moving relative to the hemispherical head. The hardening of the bone cement or other bio-compatible material in small cavities formed on the lower surface of the cap and the facing surface of the hemispherical head prevents axial rotation of the hemispherical head within the housing. A humeral head of size and shape corresponding to the trial head is impacted on the housing after the bone cement or other bio-compatible material has hardened.

A third preferred embodiment of modular humeral head assembly is similar to the first embodiments in various aspects. This embodiment has a housing shaped generally like a hollow cylinder. Housing has an inner surface that takes the form of a stepped cylinder having four different diameters. The central longitudinal axis of the inner surface and the central longitudinal axis of the outer surface are parallel to each other and offset from each other by a fixed distance. A cap is insertable in housing and has three holes that run from top surface to bottom surface. A screw may be inserted in each hole. A cylindrical post projects from the bottom of cap. The assembly includes an intermediate piece having a hemispherical head at one end of a tapered shaft. A top surface of the hemispherical head has three hemi-cylindrical cutouts. Hemi-cylindrical cutouts are facing holes such that if screws are advanced in holes, each screw will contact one hemi-cylindrical cutout. Intermediate piece has a blind hole in its center. Hole is shaped to allow insertion of the cylindrical post. The cylindrical post is loose in hole, thereby allowing limited relative motion between cap and intermediate piece. The assembly also includes a spherical seat ring. Spherical seat ring has an inner spherical surface that mates with spherical surface of hemispherical head to form a joint that allows rotational movement between intermediate piece and spherical seat ring. Spherical seat ring has an outer surface that is sized to mate with the cylindrical surfaces on the inside of housing. Trial head may be used with the present embodiment in same manner as discussed previously. The optimum position for the prosthesis is determined in a manner similar to one described in connection with the first embodiment.

The modular humeral head systems described above may be made available as a kit. The kit would contain a set of trial heads and a corresponding set of humeral heads. The kit may also contain humeral stems of various sizes.

Additional objects and advantages of the invention will become apparent to those skilled in the art upon reference to the detailed description taken in conjunction with the provided figures.

BRIEF DESCRIPTION OF THE DRAWINGS

FIG. 1 is an isometric view of an assembly of housing and an intermediate piece of the first embodiment of a modular humeral prosthesis.

FIG. 2 is an isometric view of a cap for the first embodiment of a modular humeral prosthesis.

FIG. 3 is an isometric view of three screws for the first embodiment of a modular humeral prosthesis.

FIG. 4 is a sectional view of a humeral stem for the first embodiment of a modular humeral prosthesis.

FIG. 5 is a sectional isometric view of a humeral head for the first embodiment of a modular humeral prosthesis.

DETAILED DESCRIPTION

Figure 6:
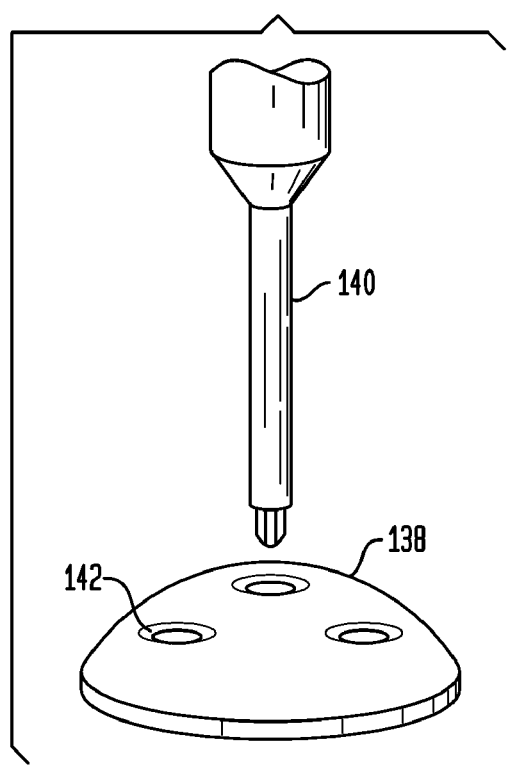
FIG. 6 is an isometric view of a trial head for the first embodiment of a modular humeral prosthesis.

FIGS. 1-5 show various parts of a first embodiment of a modular humeral head assembly. FIG. 1 shows a housing 100. Housing 100 is shaped generally like a hollow cylinder. Housing 100 has an outer surface 102 and an inner surface 104. A hemispherical socket 106 is formed on one end of inner surface 104. Threads 108 are formed on the other end of inner surface 104. Outer surface 102 has a Morse taper.

A cap 110 (FIG. 2) is attached at the threaded end of housing 100. Cap 110 has a generally cylindrical structure. The outside cylindrical surface 112 of cap 110 has threads 114. Threads 114 mate with threads 108 formed on inner surface 104. Cap 110 has a top surface 116 and a bottom surface 118. Top surface 116 and bottom surface 118 may be substantially parallel to each other and orthogonal to cylindrical surface 112. Cap 110 has three holes 120 that run from top surface 116 to bottom surface 118. Holes 120 have internal threads 122 formed on their periphery. A screw 124 (FIG. 3) may be inserted in each hole 120. The head of screw 124 is formed to allow engagement with a screw driver, for example, a hexagonal screw driver 140 (FIG. 6).

Figure 7:
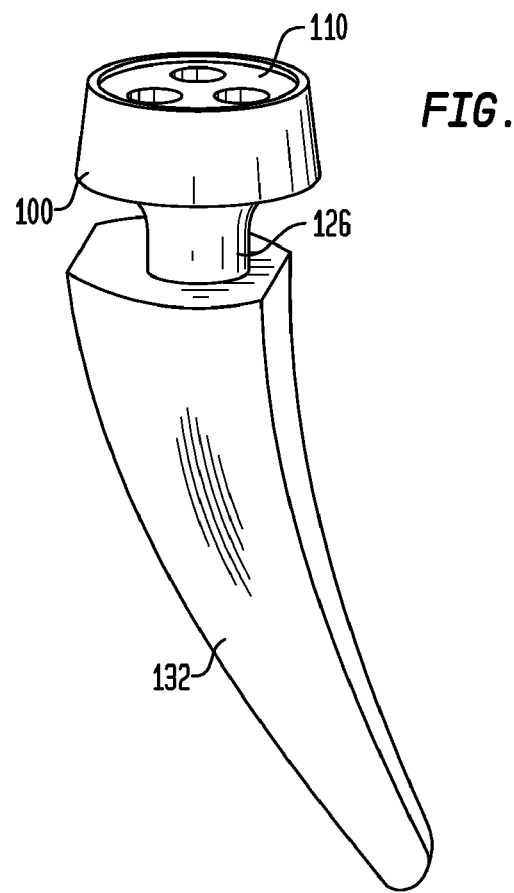
FIG. 7 is an isometric view of an assembly of the housing, intermediate piece, cap and humeral stem for the first embodiment of a modular humeral prosthesis.
Figure 12:
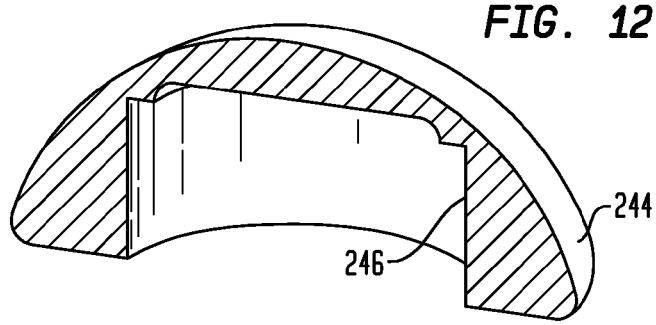
FIG. 12 is a sectional isometric view of a humeral head for the second embodiment of a modular humeral prosthesis.
Figure 10:
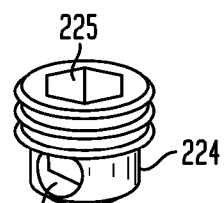
FIG. 10 is an isometric view of the screw for the second embodiment of a modular humeral prosthesis.
Figure 9:
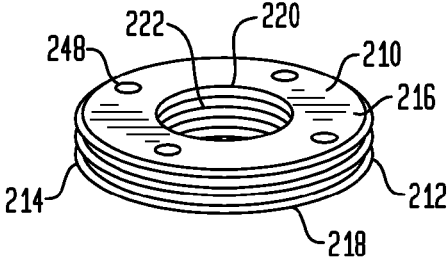
FIG. 9 is an isometric view of a cap for the second embodiment of a modular humeral prosthesis.

An intermediate piece 126 (FIG. 1) has a hemispherical head 128 at one end of a tapered shaft 129. Tapered shaft 129 has a Morse taper that matches a female taper 130 in a humeral stem 132 (FIG. 4). Humeral stem 132 may come in different size, each stem being capable of assembly with tapered shaft 129. A top surface 134 of hemispherical head 128 has three flat surfaces 136. Flat surfaces 136 may form an angle with the longitudinal axis of intermediate piece 126, for example, flat surface 136 may form an eight (8) degree angle with the longitudinal axis of intermediate piece 126. Flat surfaces 136 are facing holes 120 such that if screws 124 are advanced in holes 120, each screw 124 will contact one flat surface 136. FIG. 7 shows an assembly of intermediate piece 126, housing 100, cap 110 and humeral stem 132. Intermediate piece 126, housing 100, cap 110 and screws 124 may be factory assembled.

FIG. 6 shows a trial head 138. Trial head 138 comes in different sizes and hemispherical heights. Trial head 138 may have a hollow hemispherical shape. The inside surface of trial head 138 has a Morse taper that matches the male taper on outer surface 102 of housing 100. Trial head 138 has three holes 142 that are aligned with three screws 124 inserted in cap 110. Holes 142 provide access to screws 124 without removing trial head 138 from housing 100.

In use, cap 110 is screwed in housing 100 which in turn is attached to hemispherical head 128 via a ball-and-socket type coupling. In the assembled state, cap 110 and housing 100 are movably attached to hemispherical head 128 such that they can rotate about the hemispherical head, thereby allowing angular adjustment. The humeral bone is exposed and prepared by known surgical methods. Humeral stem 132 is inserted in the prepared medullary canal of humeral bone. Next, trial head 138 is assembled on housing 100. The matching Morse taper on housing 100 and trial head 138 fixes trial head 138 to housing 100. The assembly of trial head 138, cap 110 and housing 100 can be adjusted to be in any angular orientation about hemispherical head 128. Next, tapered shaft 129 of intermediate piece 126 is inserted in humeral stem 132 to create a modular humeral head assembly for trial reduction of the shoulder joint. With the modular humeral head assembly installed in the medullary canal, the shoulder joint is reduced. The reduced joint is evaluated for being optimal. For example, the reduced joint is evaluated for having proper muscle tension and retroversion angle. If any adjustment in the angular location of trial head 138 is needed, one or more of screws 124 are accessed through holes 142 in trial head 138 and loosened using screw driver 140. Once the desired number of screws 124 are loosened, the angular position of trial head 138 is adjusted and then screws 124 are tightened. The tightening of screws 124 fixes the angular position of trial head 138. The shoulder joint is evaluated again with the changed position of trial head 138, and the process repeated if necessary. Once an optimum position for trial head 138 is established, trial head 138 is replaced with a humeral head 144 (FIG. 5) of corresponding size and shape.

Humeral head 144 comes in different sizes and hemispherical heights. Humeral head 144 may have a hollow hemispherical shape. An inside surface 146 of Humeral head 144 has a Morse taper that matches male taper on outer surface 102 of housing 100.

Figure 24:
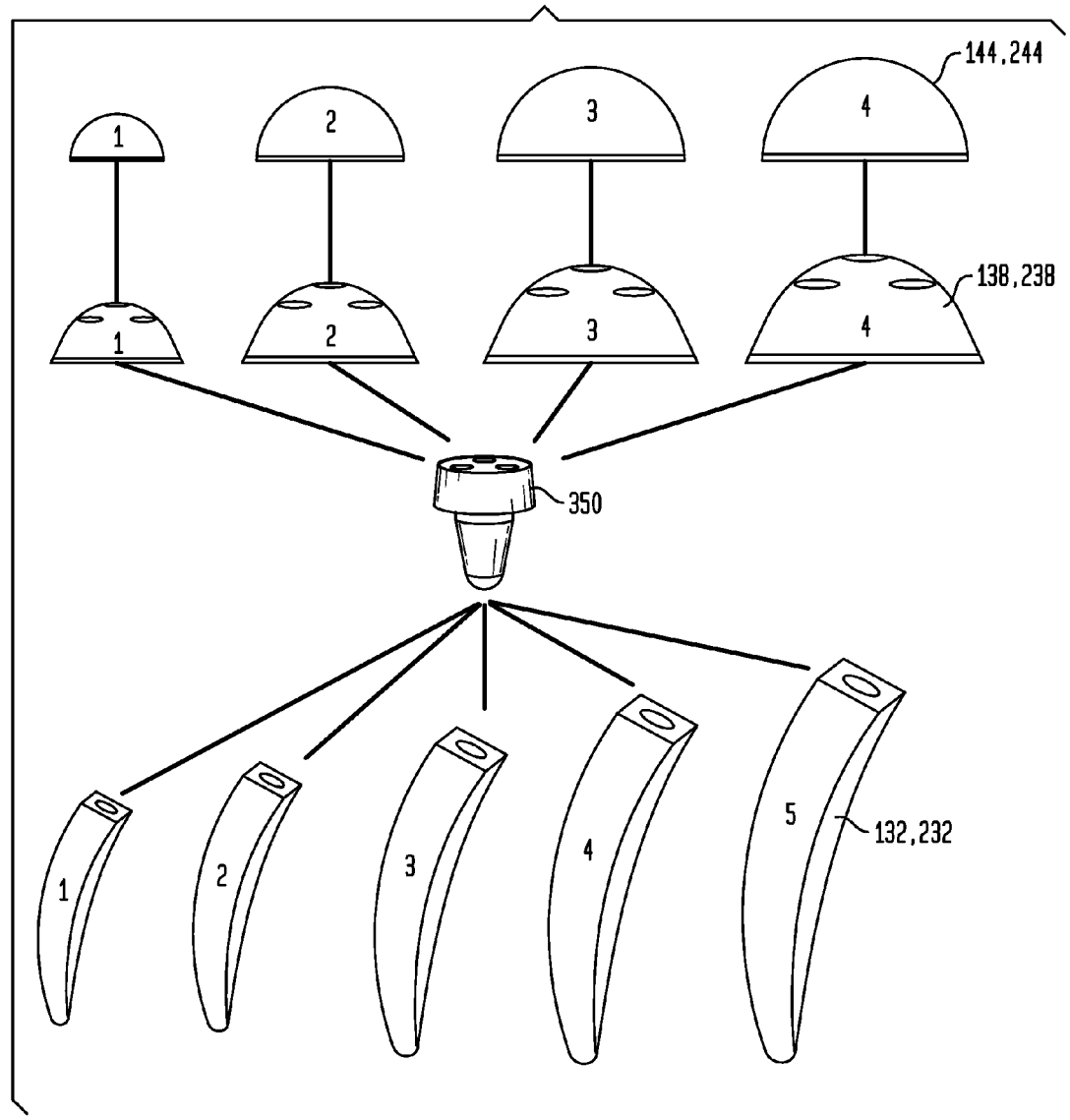
FIG. 24 shows a modular prosthesis kit of the first, second or third embodiment.

The modular humeral head system may be made available as a kit (see FIG. 24). The kit would contain a set of trial heads 138 and a corresponding set of humeral head 144. The kit may also contain humeral stems 132 of various sizes. Each humeral stem 132 may be made such that it can be assembled with tapered shaft 129 of intermediate piece 126. The housing assembly 350 shown in FIG. 24, in one embodiment, includes intermediate piece 129, housing 100, cap 110 and screws 124 assembled at the factory.

Figure 8:
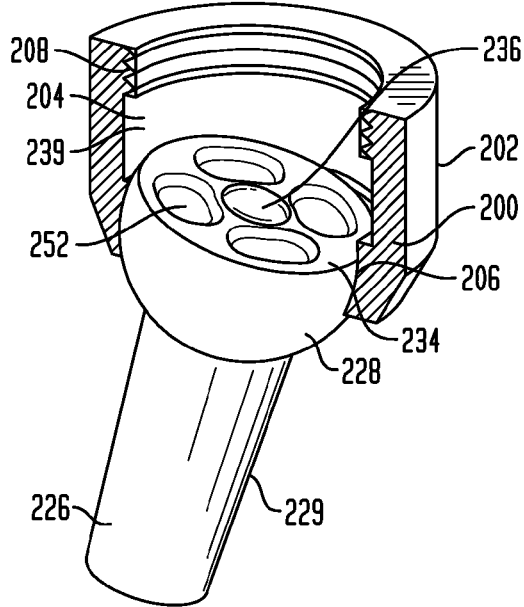
FIG. 8 is an isometric view of an assembly of housing and an intermediate piece of the second embodiment of a modular humeral prosthesis.
Figure 13:
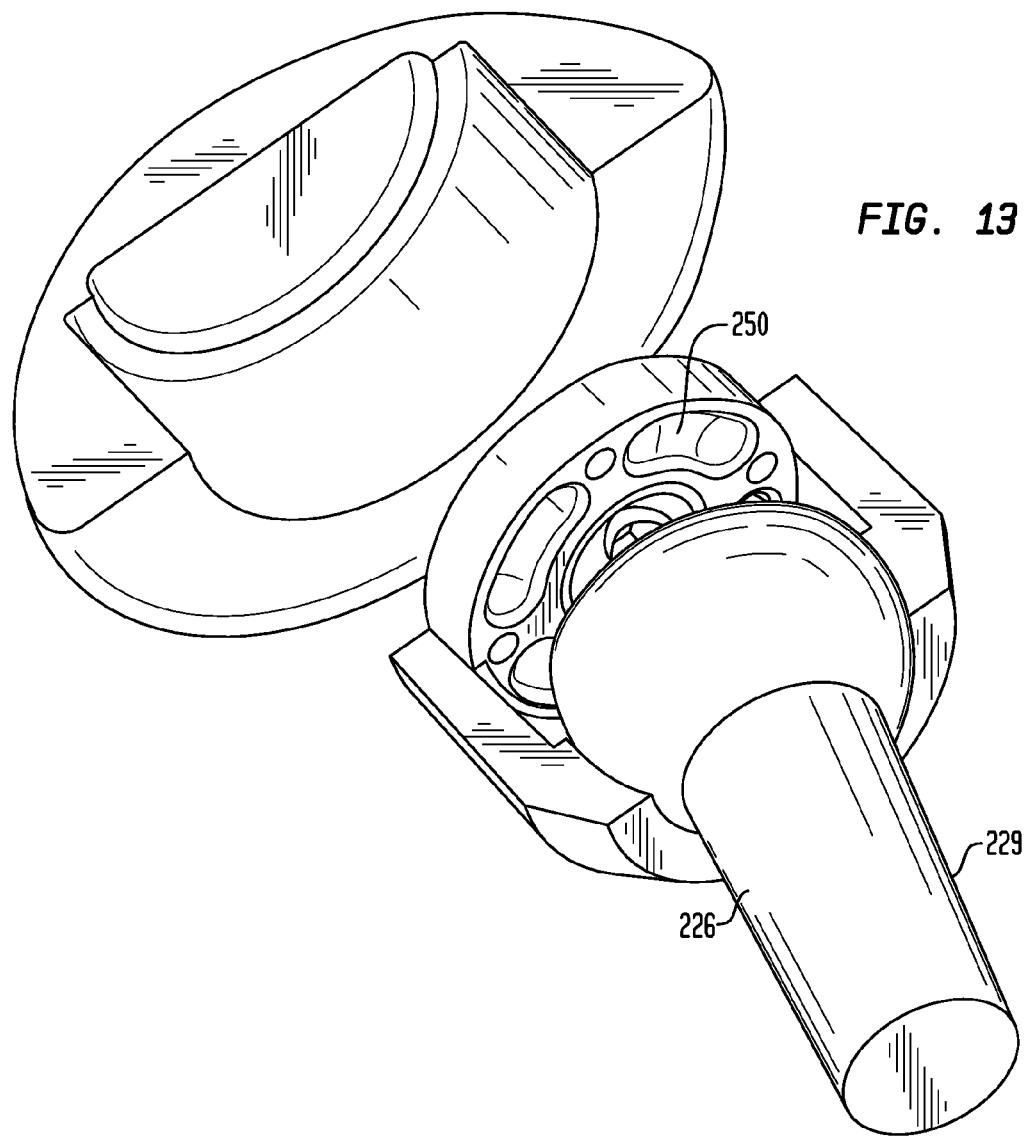
FIG. 13 is an isometric view showing the intermediate piece, cap and a portion of the humeral head for the second embodiment of a modular humeral prosthesis.

FIGS. 8-12 show various parts of a second embodiment of modular humeral head assembly. FIG. 8 shows a housing 200. Housing 200 is shaped generally like a hollow cylinder. Housing 200 has an outer surface 202 having a Morse taper, and an inner surface 204. A hemispherical socket 206 is formed on one end of inner surface 204. Threads 208 are formed on the other end of inner surface 204. The construction of housing 200 is similar to construction of housing 100 discussed previously.

A cap 210 (FIG. 9) is attached at the threaded end of housing 200. Cap 210 has a generally cylindrical structure. The outside cylindrical surface 212 of cap 210 has threads 214. Threads 214 mate with threads 208 formed on inner surface 204. Cap 210 has a top surface 216 and a bottom surface 218. Top surface 216 and bottom surface 218 may be substantially parallel to each other and orthogonal to cylindrical surface 212. Cap 210 has a hole 220 that runs from top surface 216 to bottom surface 218. Hole 220 has internal threads 222 formed on its periphery. A screw 224 (FIG. 10) may be inserted in hole 220. The head of screw 224 is formed to allow engagement with a screw driver, for example, a hexagonal screw driver 240 (FIG. 14).

Figure 11:
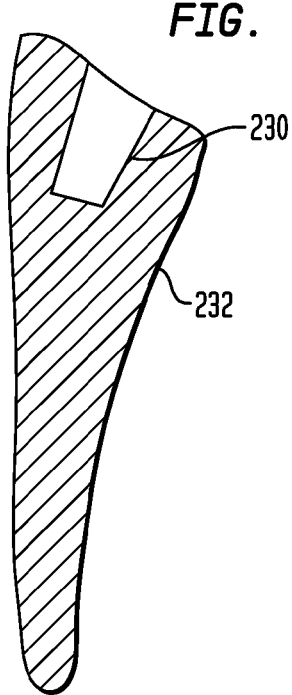
FIG. 11 is a sectional view of a humeral stem for the second embodiment of a modular humeral prosthesis.
Figure 15:
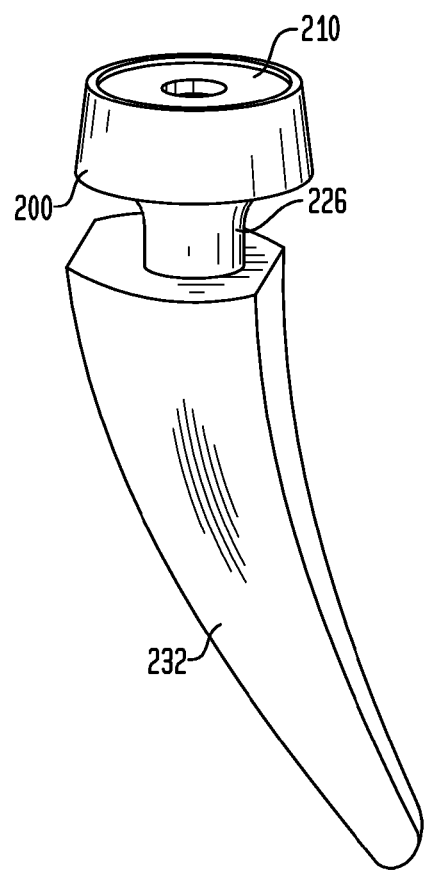
FIG. 15 is an isometric view of an assembly of the housing, intermediate piece, cap and humeral stem for the second embodiment of a modular humeral prosthesis.
Figure 16:
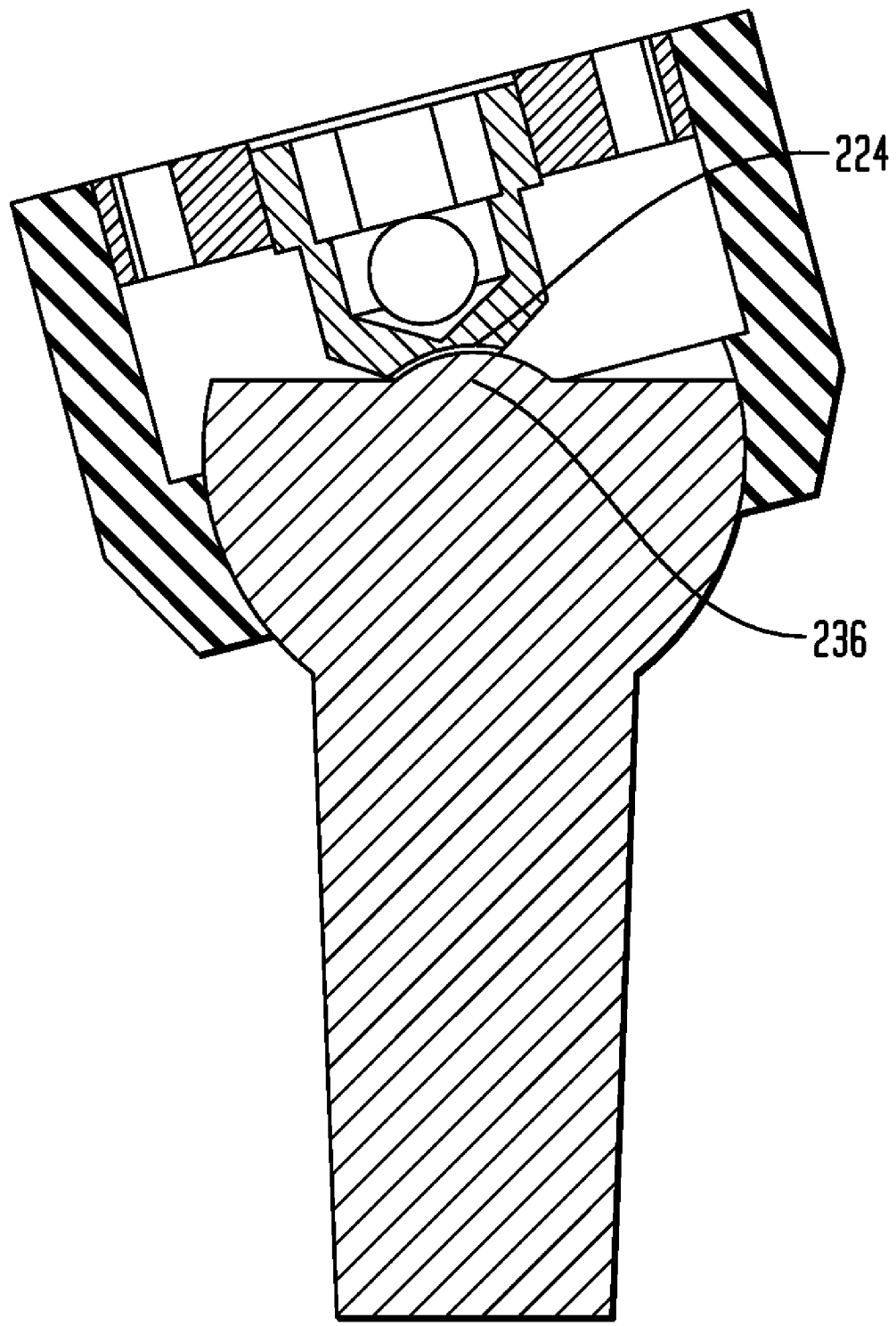
FIG. 16 is a cross sectional view of an assembly of the intermediate piece, housing, cap and a screw of the second embodiment of a modular humeral prosthesis.

An intermediate piece 226 (FIG. 8) has a hemispherical head 228 at one end of a tapered shaft 229. Tapered shaft 229 has a Morse taper that matches a female taper 230 in a humeral stem 232 (FIG. 11). Humeral stem 232 may come in different sizes, each stem being capable of assembly with tapered shaft 229. A top surface 234 of hemispherical head 228 has a shaped surface 236. Shaped surfaces 236 is facing hole 220 such that if screw 224 is advanced in hole 220, it will contact shaped surface 236. Shaped surface 236 and tip of screw 224 have complimentary shapes, for example, shaped surface 236 may be convex and the tip of screw 224 may be concave or vice versa (see FIG. 16). The complimentary surfaces on tip of screw 224 and shaped surface 236 allow them to mate in a stable manner. Since screw 224 is rigidly connected to cap 210, which in turn is rigidly connected to housing 200, tightening of screw 224 against shaped surface 236 results in fixing housing 200 relative to hemispherical head 228. However, since the contact surface between screw 224 and shaped surface 236 is not large it may be desirable to further stabilize the relative positioning of housing 200 relative to hemispherical head 228. FIG. 15 shows an assembly of intermediate piece 226, housing 200, cap 210 and humeral stem 232. Intermediate piece 226, housing 200, cap 210 and screw 224 may be factory assembled.

Figure 14:
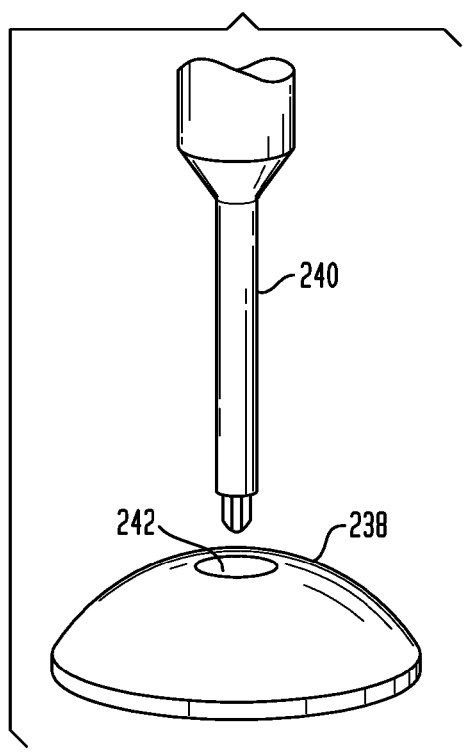
FIG. 14 is an isometric view of a trial head for the second embodiment of a modular humeral prosthesis.

FIG. 14 shows a trial head 238. Trial head 238 comes in different sizes and hemispherical heights. Trial head 238 may have a hollow hemispherical shape. The inside surface of trial head 238 has a Morse taper that matches the male taper on outer surface 202 of housing 200. Trial head 238 has a hole 242 that is aligned with screw 224 inserted in cap 210. Hole 242 provides access to screw 224 without removing trial head 238 from housing 200.

In use, cap 210 is screwed in housing 200 which in turn is attached to hemispherical head 228 via a ball-and-socket type coupling. In the assembled state, cap 210 and housing 200 are movably attached to hemispherical head 228 such that they can rotate about the hemispherical head 228, thereby allowing angular adjustment. The humeral bone is exposed and prepared by known surgical methods. Humeral stem 232 is inserted in the prepared medullary canal of humeral bone. Next, trial head 238 is assembled on housing 200. The matching Morse taper on housing 200 and trial head 238 fixes trial head 238 to housing 200. The assembly of trial head 238, cap 210 and housing 200 can be adjusted to be in any angular orientation about hemispherical head 228. Next, tapered shaft 229 of intermediate piece 226 is inserted in humeral stem 232 to create a modular humeral head assembly for trial reduction of the shoulder joint. With the modular humeral head assembly installed in the medullary canal, the shoulder joint is reduced. The reduced joint is evaluated for being optimal. For example, the reduced joint is evaluated for having proper muscle tension and retroversion angle. If any adjustment in the angular location of trial head 238 is needed, screw 224 is accessed through hole 242 in trial head 238 and loosened using screw driver 240. Once screw 224 is loosened, the angular position of trial head 238 is adjusted and then screw 224 is tightened. The tightening of screw 224 fixes the angular position of trial head 238. The shoulder joint is evaluated again with the changed position of trial head 238, and the process repeated if necessary. Once an optimum position for trial head 238 is established, trial head 238 is removed.

With trial head 238 removed, bone cement or other bio-compatible hardenable material is introduced in chamber 239 via an aperture 225. Screw 224 has aperture 225 that is in fluid communication with a chamber 239 enclosed by intermediate piece 226, housing 200 and cap 210. The bone cement or other bio-compatible material is introduced in chamber 239 under pressure. Cap 210 has one or more air bleeding holes 248 that allow air to escape from chamber 239 when pressurized bone cement or other bio-compatible material is introduced in chamber 239. The bone cement or other bio-compatible material cures in chamber 239 and turns to a hard mass. The presence of this hard mass in chamber 239 prevents housing 200 from moving relative to hemispherical head 228. Cap 210 has one or more small cavities 250 formed on bottom surface 218. Hemispherical head 228 also has small cavities 252 formed on its surface. Small cavities 250 and 252 are located in chamber 239. The bone cement or other bio-compatible material enters small cavities 250 and 252 and hardens therein upon curing. The hardening of the bone cement or other bio-compatible material in small cavities 250 and 252 prevents axial rotation of hemispherical head within housing 200. A humeral head 244 of size and shape corresponding to trial head 238 is impacted on housing 200 after the bone cement or other bio-compatible material has hardened.

Humeral head 244 comes in different sizes and hemispherical heights. Humeral head 244 may have a hollow hemispherical shape. The inside surface 246 of Humeral head 244 has a Morse taper that matches male taper on outer surface 202 of housing 200.

The modular humeral head system described above may be made available as a kit (see FIG. 24). The kit would contain a set of trial heads 238 and a corresponding set of humeral heads 244. The kit may also contain humeral stems 232 of various sizes. Each humeral stem 232 may be made such that it can be assembled with tapered shaft 229 of intermediate piece 226. The housing assembly 350 shown in FIG. 24, in one embodiment, includes intermediate piece 226, housing 200, cap 210 and screw 224 assembled at the factory.

Figure 17:
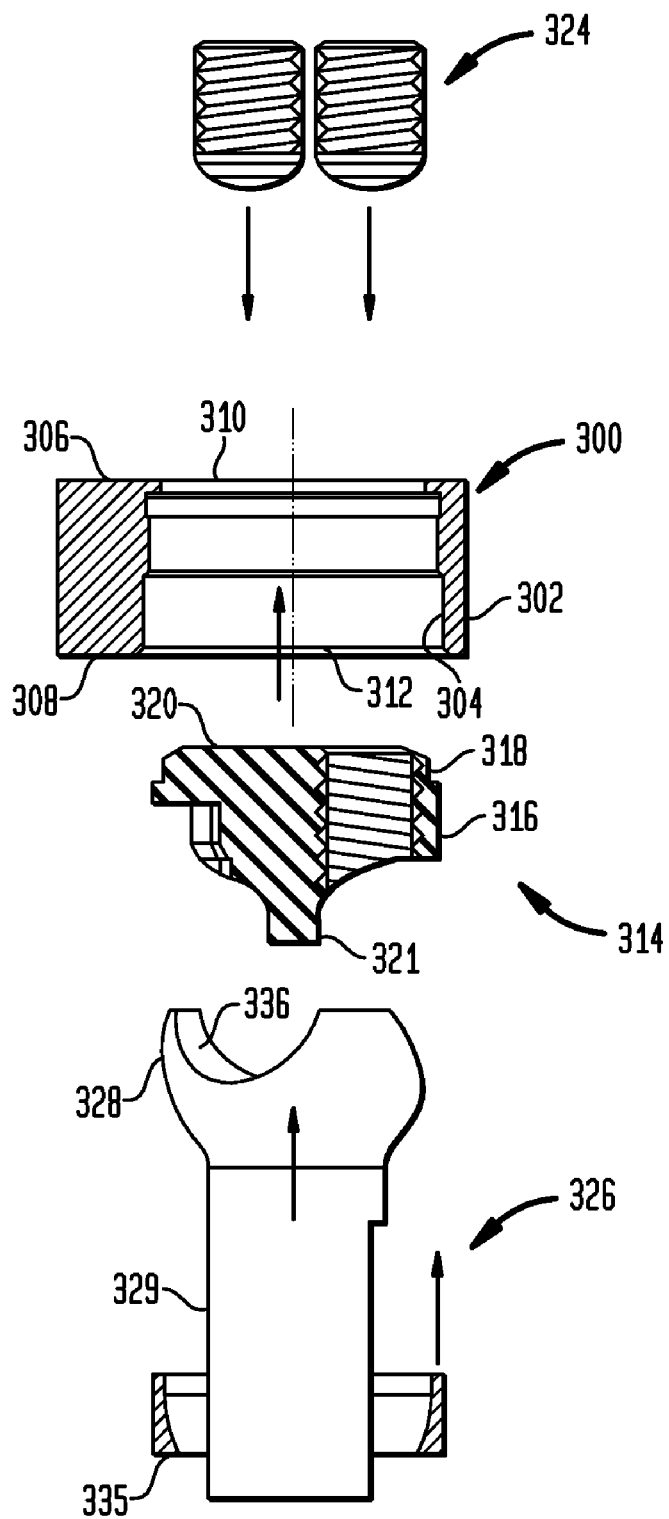
FIG. 17 is a view of an assembly of a housing, an intermediate piece, a seat ring, a cap and screws of the third embodiment of a modular humeral prosthesis.
Figure 18:
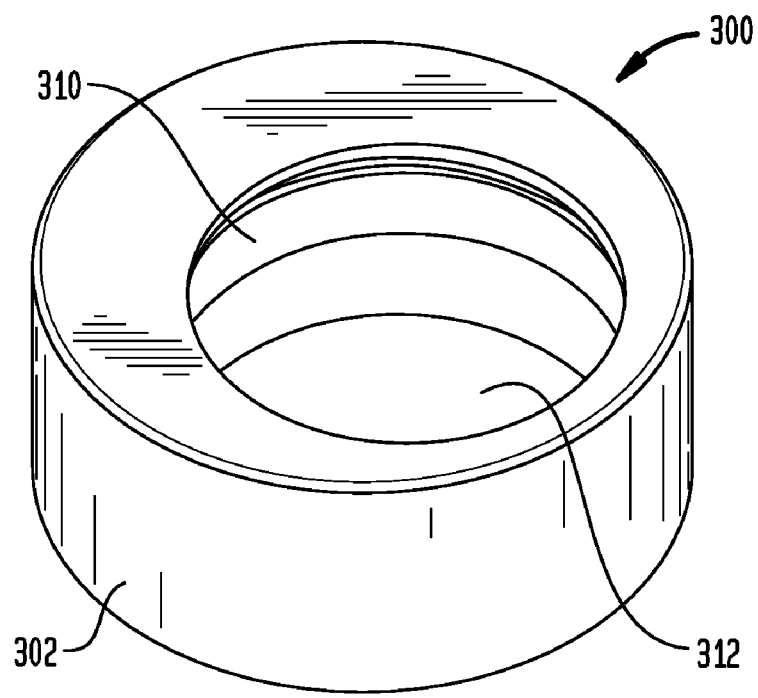
FIG. 18 is an isometric view of the housing shown in FIG. 17.

FIG. 17 shows various parts of a third preferred embodiment of modular humeral head assembly. FIGS. 17 and 18 show a housing 300. Housing 300 is shaped generally like a hollow cylinder. Housing 300 has an outer surface 302 and an inner surface 304. Inner surface 304 takes the form of a stepped cylinder having four different diameters. Housing 300 also has a top surface 306 and a bottom surface 308. Top surface 306 has an opening 310 and bottom surface 308 has an opening 312. Opening 310, opening 312, are coaxial. The central longitudinal axis of opening 310 and opening 312 and the central longitudinal axis of the outer surface 302 are parallel to each other and off set from each other by a fixed distance, for example 2 millimeter. Outer surface 302 has a Morse taper.

Figure 19:
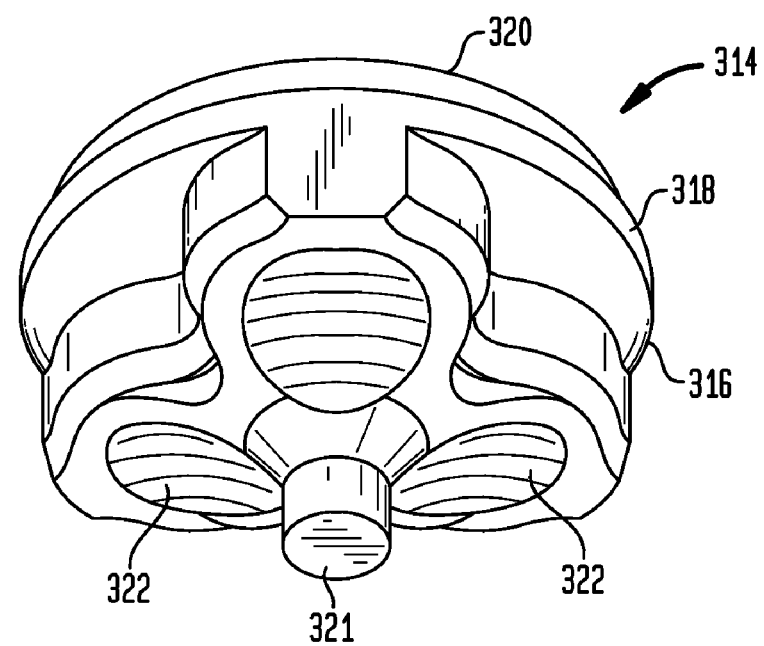
FIG. 19 is an isometric view of the cap shown in FIG. 17.
Figure 20:
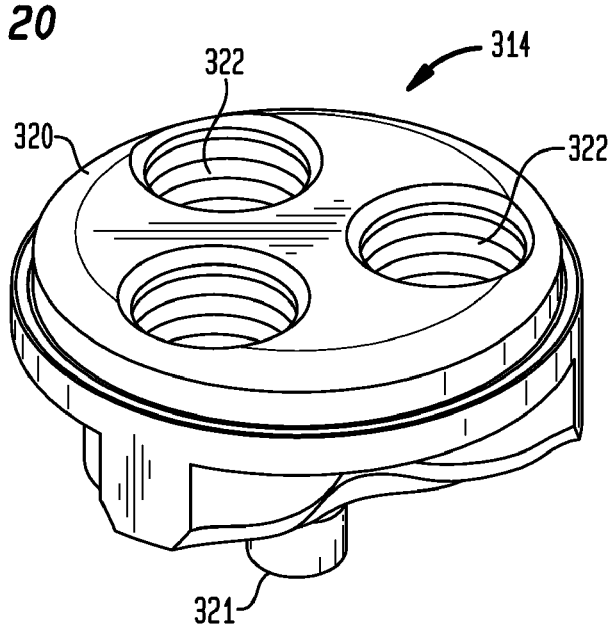
FIG. 20 is another isometric view of the cap of FIG. 17 showing the top surface of the cap.

A cap 314 (FIGS. 17, 19 and 20) is insertable in housing 300 through opening 312. Cap 314 has a generally cylindrical structure. Outside cylindrical surfaces 316 and 318 mate with the stepped cylindrical surfaces on the inside of housing 300. A top surface 320 of cap 314 projects out from opening 310 in housing 300. Cap 314 has a top surface and a bottom surface and three holes 322 that run from top surface to bottom surface. Holes 322 have internal threads formed on their periphery. A screw 324 may be inserted in each hole 322. The head of screw 324 is formed to allow engagement with a screw driver, for example, a hexagonal screw driver 140 (FIG. 6). A cylindrical post 321 projects from the bottom of cap 314. Post 321 may be of any suitable shape, for example, it may have a square or an oval cross section.

Figure 21:
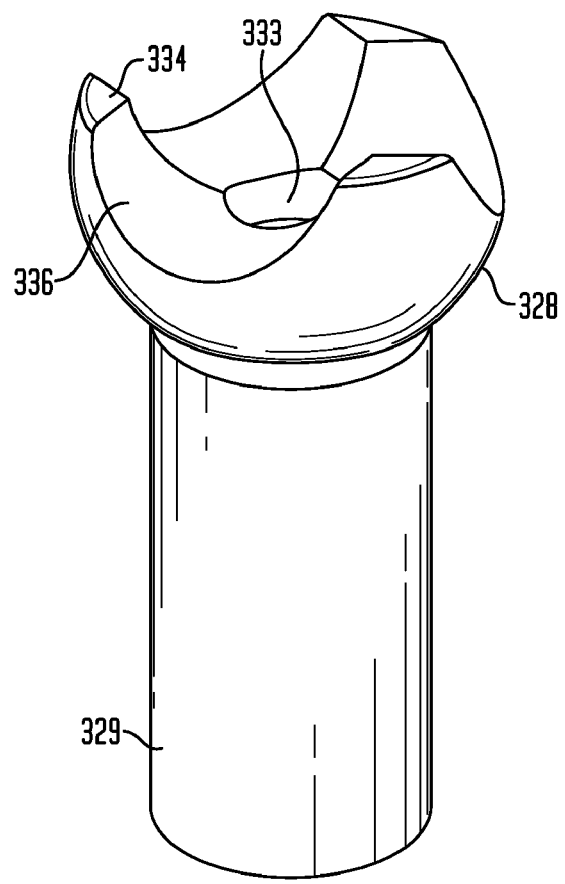
FIG. 21 is an isometric view of the intermediate piece shown in FIG. 17.

An intermediate piece 326 (FIGS. 17 and 21) has a hemispherical head 328 at one end of a tapered shaft 329. Tapered shaft 329 has a Morse taper that matches a female taper 130 in a humeral stem 132 (FIG. 4). Humeral stem 132 may come in different size, each stem being capable of assembly with tapered shaft 329. A top surface 334 of hemispherical head 328 has three hemi-cylindrical cutouts 336. Hemi-cylindrical cutouts 336 are facing holes 322 such that if screws 324 are advanced in holes 322, each screw 324 will contact one hemi-cylindrical cutout 336. Intermediate piece 326 has a blind hole 333 in its center. Hole 333 is shaped to allow insertion of post 321. Post 321 is loose in hole 333, thereby allowing limited relative motion between cap 314 and intermediate piece 326.

Figure 22:
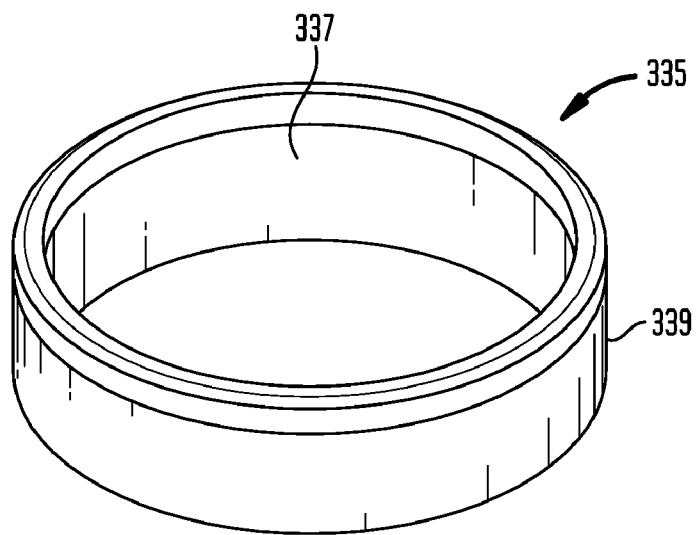
FIG. 22 is an isometric view of the spherical seat ring shown in FIG. 17.

FIGS. 17 and 22 show a spherical seat ring 335. Spherical seat ring 335 has an inner spherical surface 337 that mates with spherical surface of hemispherical head 328 to form a joint that allows rotational movement between intermediate piece 326 and spherical seat ring 335. Spherical seat ring 335 has an outer surface 339 that is sized to mate with the cylindrical surfaces on the inside of housing 300.

FIG. 6 shows a trial head 138. Trial head 138 may be used with the present embodiment in same manner as discussed previously.

Figure 23:
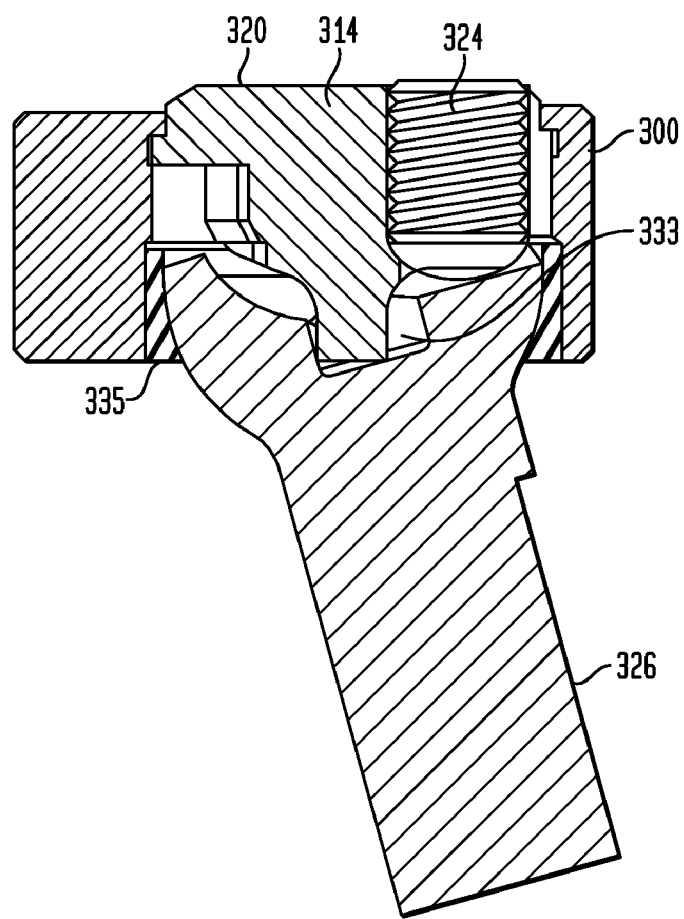
FIG. 23 is a cross sectional view of an assembly of a housing, an intermediate piece, a seat ring, a cap and screws of the third embodiment of a modular humeral prosthesis.

FIG. 23 shows an assembly of intermediate piece 326, housing 300, screws 324, cap 314 and spherical seat ring 335. Intermediate piece 326, housing 300, cap 314 and spherical seat ring 335 are factory assembled. To assemble, spherical seat ring 335 is passed over the stem of tapered shaft 329 to bring its inner spherical surface 337 in contact with the spherical surface of hemispherical head 328. Next, cap 314 is inserted in housing 300 which in turn is attached to spherical seat ring 335 via laser welding. In the assembled state, cap 314 and housing 300 are movably attached to hemispherical head 328 via spherical seat ring 335 such that they can rotate about the hemispherical head 328, thereby allowing angular adjustment. However, post 321 touches the walls of hole 333 when head 328 is moved beyond a certain limit, thereby acting as a limit stop on the movement of head 328. The humeral bone is exposed and prepared by known surgical methods. Humeral stem 132 is inserted in the prepared medullary canal of humeral bone. Next, trial head 138 is assembled on housing 300. The matching Morse taper on housing 300 and trial head 138 fixes trial head 138 to housing 300. The assembly of trial head 138, cap 314 and housing 300 can be adjusted to be in any angular orientation about hemispherical head 328. Next, tapered shaft 329 of intermediate piece 326 is inserted in humeral stem 132 to create a modular humeral head assembly for trial reduction of the shoulder joint. With the modular humeral head assembly installed in the medullary canal, the shoulder joint is reduced. The reduced joint is evaluated for being optimal. For example, the reduced joint is evaluated for having proper muscle tension and retroversion angle. If any adjustment in the angular location of trial head 138 is needed, one or more of screws 324 are accessed through holes 142 in trial head 138 and loosened using screw driver 140. Once the desired number of screws 324 are loosened, the angular position of trial head 138 is adjusted and then screws 324 are tightened. The tightening of screws 324 fixes the angular position of trial head 138. The shoulder joint is evaluated again with the changed position of trial head 138, and the process repeated if necessary. Once an optimum position for trial head 138 is established, trial head 138 is replaced with a humeral head 144 (FIG. 5) of corresponding size and shape.

Humeral head 144 comes in different sizes and hemispherical heights. Humeral head 144 may have a hollow hemispherical shape. An inside surface 146 of Humeral head 144 has a Morse taper that matches male taper on outer surface 302 of housing 300. The housing assembly 350 shown in FIG. 24, in one embodiment, includes intermediate piece 329, housing 300, cap 314, spherical seat ring 335 and screws 324 assembled at the factory.

The modular humeral head system may be made available as a kit (see FIG. 24). The kit would contain a set of trial heads 138 and a corresponding set of humeral head 144. The kit may also contain humeral stems 132 of various sizes. Each humeral stem 132 may be made such that it can be assembled with tapered shaft 329 of intermediate piece 326.

There have been described and illustrated herein modular prosthetic shoulder components. While particular embodiments of the invention have been described, it is not intended that the invention be limited thereto, as it is intended that the invention be as broad in scope as the art will allow and that the specification be read likewise. For example, as described above, the components of the invention may also be advantageously used in other prosthetic joints such as prosthetic hip joints.

It will therefore be appreciated by those skilled in the art that yet other modifications could be made to the provided invention without deviating from its spirit and scope as so claimed.

The invention claimed is:

1. A prosthetic system comprising:
    a housing having a first end and a second end;
    an intermediate piece having a third end and a fourth end, the third end being connected to the second end of the housing;
    a cap connected to the first end of the housing;
    at least one screw hole formed in the cap and having an internal thread;
    a screw inserted in the screw hole and configured to threadedly engage the internal thread of the at least one screw hole; and
    a trial head attached to the first end of the housing, the trial head having at least one opening alignable with one of the screw holes in the cap;
    a head, the head being attachable to the first end of the housing in place of the trial head;
    a first taper formed on an outside of the housing;
    a second taper matching the first taper, the second taper being formed on an inside of the head;
    a socket formed at the second end of the housing;
    a matching spherical surface formed at the third end of the intermediary piece; and
    a surface formed on the third end of the intermediary piece, the surface located so that when the screw is advanced it contacts the surface.

2. The prosthetic system of claim 1, wherein the housing is adapted to pivot around the third end of the intermediary piece to position the head in an optimum position and the head is capable of being locked in the optimum position.

3. The prosthetic system of claim 1, further comprising a first opening formed near the first end of the housing for filling an interior of the housing with an encapsulant.

4. The prosthetic system of claim 3, wherein the first opening is formed in the screw.

5. The prosthetic system of claim 3, further comprising at least one second opening formed near the first end of the housing to allow the air to escape during encapsulation.

6. The prosthetic system of claim 5, further comprising at least one first cavity formed on the third end of the intermediary piece.

7. The prosthetic system of claim 6, further comprising at least one second cavity formed on the cap.

8. The prosthetic system of claim 5, further comprising at least one first projection formed on the third end of the intermediary piece.

9. The prosthetic system of claim 8, further comprising a surface formed on a leading edge of the screw, a shape of the surface being complimentary to a shape of the projection.

10. The prosthetic system of claim 9, further comprising:
    a stem having a fifth end and a sixth end, the fifth end being attached to the fourth end of the intermediary piece;
    a tapered bore formed at the fifth end of the stem; and
    a tapered surface matching the tapered bore at the fifth end formed at the fourth end of the intermediary piece.

11. A prosthetic device comprising:
    a housing having a first end and a second end;
    an intermediary piece having a third end and a fourth end, the third end being connected to the second end of the housing;
    at least three screws projecting in a space between the intermediary piece and the housing; and
    a head attached to the first end of the housing and configured to surround at least a portion of the housing, wherein the housing is adapted to pivot around the third end of the intermediary piece to position the head in an optimum position and the head is locked in the optimum position upon tightening of the screws.

12. The prosthetic device of claim 11, further comprising:
    a cap, the cap being mounted on the housing to enclose a space between the intermediary piece and the housing and having three threaded holes for insertion of the screws.

13. The prosthetic device of claim 11, further comprising:
    a first taper formed on an outside of the housing; and
    a second taper matching the first taper, the second taper being formed on an inside of the head.

14. The prosthetic device of claim 13, further comprising:
    a socket formed at the second end of the housing; and
    a matching spherical surface formed at the third end of the intermediary piece.

15. The prosthetic device of claim 14, further comprising at least one surface formed on the third end of the intermediary piece, the surface located so that when at least one of the screws is advanced it contacts the surface.

16. The prosthetic device of claim 15, further comprising:
    a stem having a fifth end and a sixth end, the fifth end being attached to the fourth end of the intermediary piece;
    a tapered bore formed at the fifth end of the stem; and a tapered surface matching the tapered bore at the fifth end formed at the fourth end of the intermediary piece.

17. The prosthetic device of claim 11, wherein the head is a trial head.

18. The prosthetic device of claim 17, wherein the trial head has at least one opening that allows access to the screw.

19. A prosthetic device comprising:
an intermediary piece having a tapered shaft portion;
a stem, the tapered shaft portion being inserted in a matching tapered portion of the stem;
a trial head mounted on the intermediary piece, wherein once a trial reduction results in optimum placement of the prosthetic device, only the trial head is replaced by a humeral head;
a first taper formed on an outside surface of a housing;
a second taper matching the first taper, the second taper being formed on an inside surface of the trial head;
a socket formed on an inside surface of the housing;
a matching spherical surface formed on the intermediary piece;
at least one flat surface formed on the spherical surface of the intermediary piece;
a cap, the cap being screwed to the housing; and
at least one screw mounted on the cap such that when the screw is advanced it contacts the flat surface.

20. A prosthetic system comprising:
a housing having a cylindrical outside surface having a first longitudinal axis and a cylindrical bore having a second longitudinal axis, the first and the second longitudinal axis being parallel to each other and offset from each other by a predetermined distance;
an intermediary piece having a first end and a second end, the first end having a spherical surface;
a seat ring having a spherical inside surface adapted to mate with the spherical surface of the intermediary piece and an outside surface adapted to attach to the housing;
a cap inserted in the housing;
at least three screw holes formed in the cap;
a screw inserted in each of the screw holes;
a trial head attached to a first end of the housing, the trial head having at least one opening alignable with one of the screw holes in the cap; and
a head, the head being attachable to the first end of the housing in place of the trial head.

21. The prosthetic system of claim 20, further comprising:
a beam projecting from a lower surface of the cap; and
a blind hole formed in the intermediary piece, wherein the beam touches the walls of the blind hole when the trial head is rotated beyond a certain limit, thereby limiting the rotation of the trial head.

22. The prosthetic system of claim 21, wherein the housing is adapted to pivot around the intermediary piece to position the head in an optimum position and the head is capable of being locked in the optimum position.

23. The prosthetic system of claim 21, further comprising:
a first taper formed on the outside of the housing; and
a second taper matching the first taper, the second taper being formed on an inside of the head.

24. The prosthetic system of claim 23, further comprising at least one hemi-cylindrical surface formed on the first end of the intermediary piece, the hemi-cylindrical surface located so that when at least one of the screws is advanced it contacts the hemi-cylindrical surface.

25. The prosthetic system of claim 24, further comprising:
a stem having a third end and a fourth end, the third end being attached to the second end of the intermediary piece;
a tapered bore formed at the third end of the stem; and
a tapered surface matching the tapered bore at the third end formed at the second end of the intermediary piece.

26. A prosthetic device comprising:
a housing having a first end and a second end;
an intermediary piece having a third end and a fourth end, the third end having a spherical surface;
a seat ring having a spherical inside surface mated with the spherical surface of the intermediary piece and an outside surface attached to the housing;
at least three screws projecting in a space between the intermediary piece and the housing; and
a head attached to the first end of the housing and configured to surround at least a portion of the housing, wherein the housing is adapted to pivot around the intermediary piece to position the head in an optimum position and the head is locked in the optimum position upon tightening of the screws.

27. The prosthetic device of claim 26, wherein the housing includes a cylindrical outside surface having a first longitudinal axis and a cylindrical bore having a second longitudinal axis, the first and the second longitudinal axis being parallel to each other and offset from each other by a predetermined distance.

28. The prosthetic device of claim 27, further comprising a cap, the cap being mounted on the housing and having three threaded holes for insertion of the screws.

29. The prosthetic device of claim 27, further comprising:
a first taper formed on an outside of the housing; and
a second taper matching the first taper, the second taper being formed on an inside of the head.

30. The prosthetic device of claim 29, further comprising at least one hemi-cylindrical surface formed on the third end of the intermediary piece, the hemi-cylindrical surface located so that when at least one of the screws is advanced it contacts the hemi-cylindrical surface.

31. The prosthetic device of claim 30, further comprising:
a stem having a fifth end and a sixth end, the fifth end being attached to the fourth end of the intermediary piece;
a tapered bore formed at the fifth end of the stem; and
a tapered surface matching the tapered bore at the fifth end formed at the fourth end of the intermediary piece.

32. The prosthetic device of claim 27, wherein the head is a trial head.

33. The prosthetic device of claim 30, wherein the trial head has at least one opening that allows access to the screw.

* * * * *